(12) United States Patent
Barker et al.

(10) Patent No.: US 11,400,270 B2
(45) Date of Patent: Aug. 2, 2022

(54) DELIVERY ADAPTER

(71) Applicant: MicroVention, Inc., Aliso Viejo, CA (US)

(72) Inventors: Pete Barker, Bonsall, CA (US); Jonathan Lam, Anaheim Hills, CA (US); Scott Pool, Laguna Hills, CA (US); Frida San, Long Beach, CA (US); Edgar Villanueva, Oceanside, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 320 days.

(21) Appl. No.: 15/889,468

(22) Filed: Feb. 6, 2018

(65) Prior Publication Data
US 2018/0221640 A1     Aug. 9, 2018

Related U.S. Application Data

(60) Provisional application No. 62/455,379, filed on Feb. 6, 2017.

(51) Int. Cl.
*A61M 39/02* (2006.01)
*A61M 3/00* (2006.01)
*A61M 25/00* (2006.01)
*A61M 5/34* (2006.01)
(Continued)

(52) U.S. Cl.
CPC .......... *A61M 39/0247* (2013.01); *A61M 3/00* (2013.01); *A61M 5/345* (2013.01); *A61M 25/0097* (2013.01); *A61B 17/12186* (2013.01); *A61M 2039/0205* (2013.01); *A61M 2039/027* (2013.01); *A61M 2039/0258* (2013.01); *A61M 2039/0276* (2013.01);
(Continued)

(58) Field of Classification Search
CPC .. A61M 2039/0009; A61M 2039/1077; A61M 2039/1027; A61M 2039/1083; A61M 2039/1088; A61M 2039/1094; A61M 39/10; A61M 39/105; A61M 2005/3206; A61M 5/343; A61M 5/34; A61M 5/3293
See application file for complete search history.

(56) References Cited

U.S. PATENT DOCUMENTS 4,710,171 A * 12/1987 Rosenberg ............ A61M 25/06
604/117
5,478,331 A 12/1995 Heflin et al.
5,810,869 A 9/1998 Kaplan et al.
(Continued)

FOREIGN PATENT DOCUMENTS

CN 106029157 A 10/2016
DE 1491866 A1 10/1969
(Continued)

OTHER PUBLICATIONS

WIPO, U.S. International Search Authority, International Search Report and Written Opinion dated May 31, 2018 in International Patent Application No. PCT/US2018/016959, 10 pages.
(Continued)

*Primary Examiner* — Dung T Ulsh
(74) *Attorney, Agent, or Firm* — Inskeep IP Group, Inc.

(57) ABSTRACT

A delivery adapter which may be used as an interface between a syringe and a catheter hub is described.

18 Claims, 19 Drawing Sheets

(51) Int. Cl.
*A61M 39/10* (2006.01)
*A61B 17/12* (2006.01)

(52) U.S. Cl.
CPC ............ *A61M 2039/0282* (2013.01); *A61M 2039/0288* (2013.01); *A61M 2039/1077* (2013.01)

(56) References Cited

U.S. PATENT DOCUMENTS

| | | | | |
|---|---|---|---|---|
| 6,146,373 | A * | 11/2000 | Cragg | A61B 17/12022 604/19 |
| 6,511,472 | B1 * | 1/2003 | Hayman | A61M 25/0097 604/533 |
| 6,695,814 | B2 | 2/2004 | Greene et al. | |
| 2003/0149395 | A1 * | 8/2003 | Zawacki | A61M 1/3653 604/40 |
| 2005/0137500 | A1 * | 6/2005 | Wingler | A61B 10/0045 600/562 |
| 2014/0039267 | A1 * | 2/2014 | Seex | A61B 90/06 600/206 |
| 2014/0039534 | A1 * | 2/2014 | Geist | A61B 17/3472 606/172 |
| 2015/0174389 | A1 * | 6/2015 | Lam | A61M 39/10 604/500 |

FOREIGN PATENT DOCUMENTS

| | | |
|---|---|---|
| JP | 2017-503574 A | 2/2017 |
| WO | WO 2008/153019 A1 | 12/2008 |
| WO | WO 2015/095815 A1 | 6/2015 |

OTHER PUBLICATIONS

China Patent Office, Office Action dated Apr. 1, 2021 with English translation in Chinese Patent Application No. 2018800152320, 11 pages.
European Patent Office, Supplementary Extended European Search Report dated Aug. 10, 2020 in European Patent Application No. 18747395.4, 9 pages.
Japan Patent Office, Office Action dated Mar. 15, 2022 with English translation in Japanese Patent Application No. JP2019-542623, 11 pages.

* cited by examiner

DELIVERY ADAPTER

RELATED APPLICATIONS

This application claims priority to U.S. Provisional Application Ser. No. 62/455,379 filed Feb. 6, 2017 entitled Delivery Adapter, which is hereby incorporated herein by reference in its entirety.

BACKGROUND OF THE INVENTION

A delivery adapter may be used as an interface between a syringe and a catheter hub. The syringe may contain a liquid material, in particular a high viscosity liquid material such as liquid embolic. Liquid embolic can be thought of as biocompatible glue which can be used to fill various vascular malformations such as aneurysm, arteriovenous malformation, fistula, or other malformations. Liquid embolic can also be used for various occlusive purposes such as vessel shutdown, fallopian tube occlusion, or occlusion of the peripheral vasculature. The delivery adapter helps to minimize or even eliminate altogether the dilution of the viscous liquid material in the catheter used to deliver said viscous liquid material to a treatment site within the vasculature.

SUMMARY OF THE INVENTION

A delivery adapter is described.

In one embodiment a delivery adapter includes a proximal connector, distal connector, micro-tube, and bridging piece.

In another embodiment a delivery adapter includes a proximal connector, distal connector, micro-tube, bridging piece, and distal rotating element.

In another embodiment a delivery adapter includes a proximal connector, micro-tube, and a distal connector movable over the microtube where the distal connector is comprised of two mating elements. In one embodiment, the distal connector further includes a seal which engages the micro-tube and prevents embolic reflux.

In another embodiment a delivery adapter includes multiple proximal connectors so that multiple syringes can be connected at the same time to the delivery adapter.

In another embodiment methods of delivering a viscous liquid material using the delivery adapter embodiments are described.

In another embodiment, a kit of parts includes embolic material and a delivery adapter.

DESCRIPTION OF EMBODIMENTS

For the description below the terms proximal and distal are used in regards to particular Figures. Please note generally the term proximal refers to items at the top part of the Figures and the term distal refers to items at the bottom part. The delivery adapter described is connected to a syringe at the top or proximal end, and to a catheter hub at the bottom or distal end. The delivery adapter, when oriented for delivery, may not necessarily sit in a vertical, top-down manner as shown in most of the figures (i.e. adapter may sit laterally, left-to-right or right-to-left depending on the delivery configuration).

Liquid embolic is generally delivered from a syringe to a catheter and then from the catheter to a location within the vasculature of a patient. The embolic material flows through the syringe, into the catheter hub, where the hub 22 includes a tapered reservoir 24 which leads into a smaller diameter channel 26 and the rest of the catheter (see FIG. 1).

Due to the tapered shape of the reservoir 24, it is possible for saline or DMSO or other fluids to remain in the reservoir after those liquids have been used to flush the catheter reservoir 24 and hub 22. When liquid embolic is subsequently delivered, the remaining flushing liquid (e.g., saline or DMSO) may mix with the liquid embolic, thereby diluting the liquid embolic. An adapter provides an interface to deliver the liquid embolic from the syringe to the catheter while minimizing contact with the catheter hub reservoir and thereby minimize or even eliminate any dilution of the liquid embolic by the flushing liquid.

Figure 1:
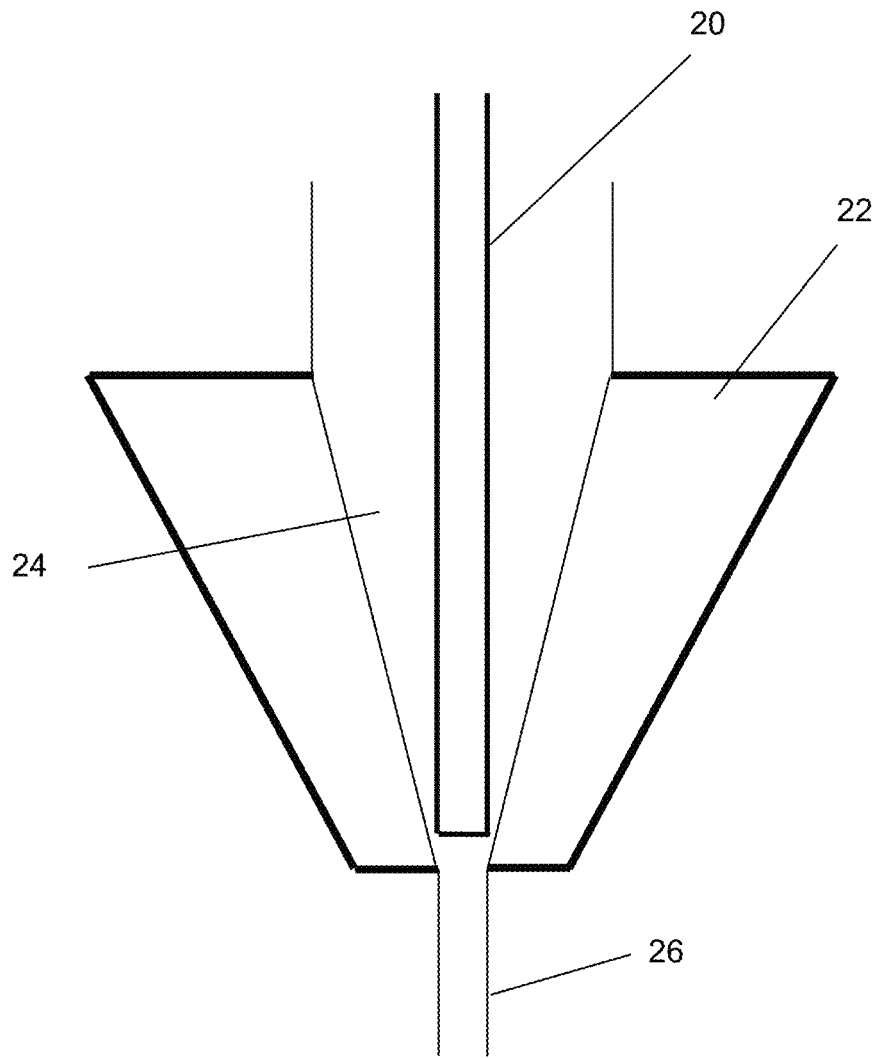
FIGS. 1-2 are schematic views of a catheter hub in accordance with the present invention.

The adapter includes a micro-tube 20 through which the liquid embolic is delivered and which sits within the catheter hub. In FIG. 1 the micro-tube 20 sits in the distal part of the catheter reservoir 24, thus minimizing potential mixing with any flushing fluid retained in the reservoir 24.

Figure 2:
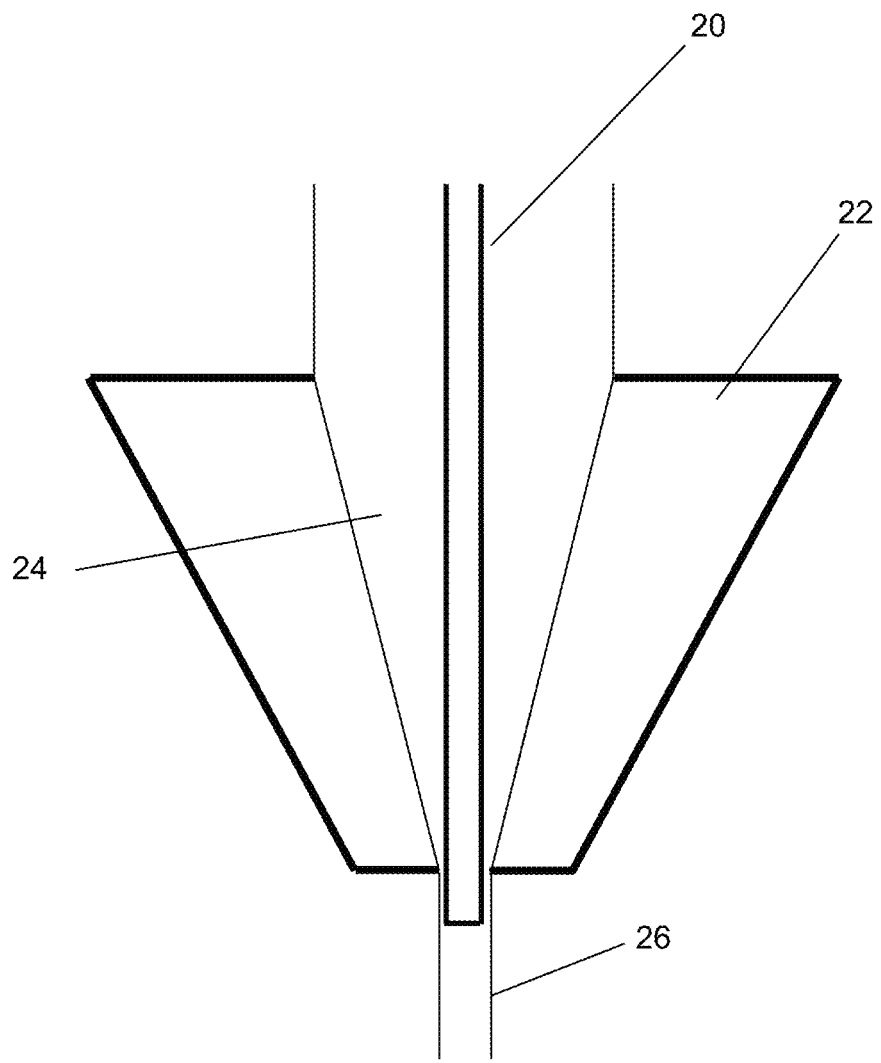

In FIG. 2, the micro-tube 20 bypasses the reservoir entirely and sits within the smaller diameter channel 26. The adapter described may adopt either configuration within the catheter hub 22 shown in FIGS. 1-2, based on the size of the reservoir 24 and length of the micro-tube 20.

Figure 3:
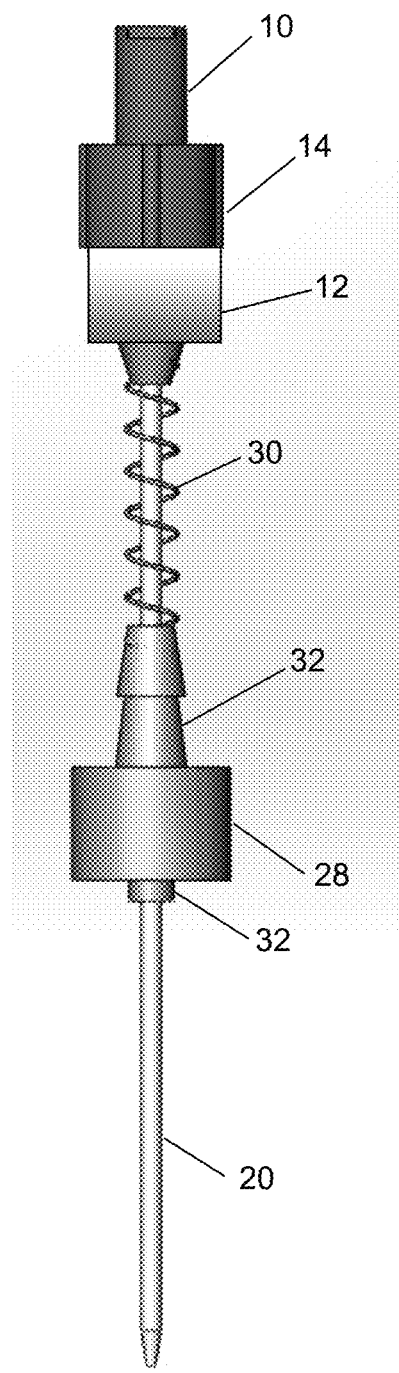
FIG. 3 is a plan view of a delivery adapter according to one embodiment of the present invention.

FIG. 3 shows an embodiment of a delivery adapter comprising a proximal connector 12, distal connector 28, micro-tube 20, and bridging piece 30 which sits between the proximal and distal connectors 12, 28. The proximal connector 12 may be made of a polymer and may include a mating section 10 in the form of a male luer which connects with the female connector of a syringe. The proximal connector 12 may also include a roughed section 14 to aid the user in gripping the adapter to screw and unscrew said adapter from the syringe. In one example the micro-tube 20 is recessed and captured within a portion of the proximal connector 12. In one example the proximal connector 12 contains a channel in which the micro-tube sits. The micro-tube 20 runs from the proximal connector 12 past distal connector 28. Bridging piece 30 sits between proximal connector 12 and distal connector 28.

In the embodiment shown in FIG. 3, the bridging piece 30 is shown as a spring which can be made of a metallic material. In one example, distal connector 28 may be made of a polymer. Distal connector 28 may include a channel 32 which runs through said connector 28. Micro-tube 20 runs through channel 32. In one example, the bridging piece 30 is glued within proximal connector 12 and sits within channels in distal connector 28. This configuration would enable rotation of the bridging piece 30 (e.g., a spring) when the distal connector 28 is not connected to the catheter hub and the user torques proximal connector 12. In one example, the distal end of micro-tube 20 extends about 5-40 mm past distal connector 28. In another example, the distal end of micro-tube 20 extends about 10-20 mm past distal connector 28. In another example, the distal end of micro-tube 20 extends about 15 mm past distal connector 28. The syringe, when mated to proximal connector 12 via mating section 10, connects directly to micro-tube 20 which sits within the proximal connector 12. Thus the syringe contents are directly transferred into the micro-tube of the adapter, and out the distal end of the micro-tube 20 into the catheter hub when the catheter hub is connected to distal connector 28.

Figure 4:
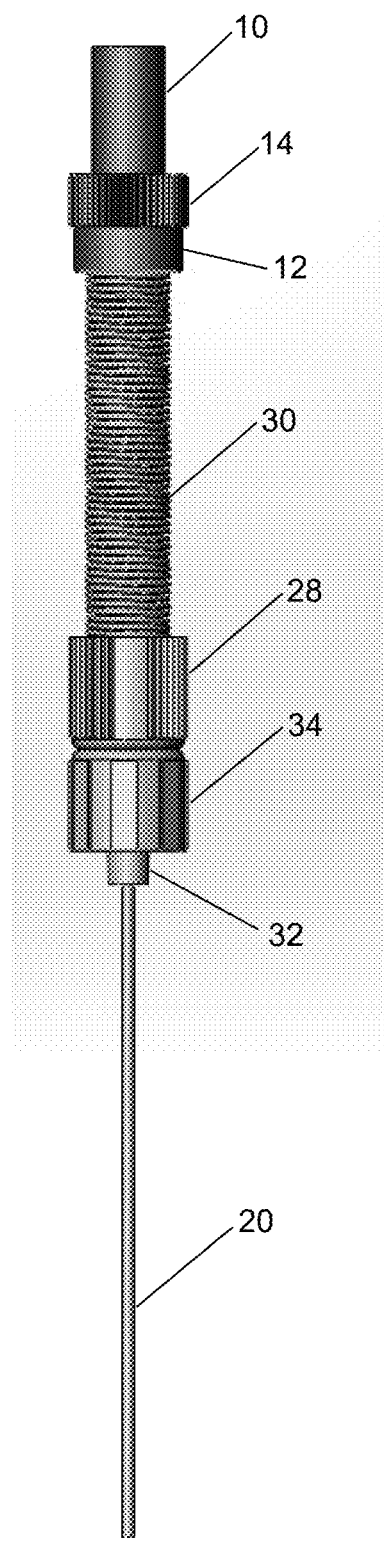
FIG. 4 is a plan view of a delivery adapter according to another embodiment of the present invention.
Figure 5:
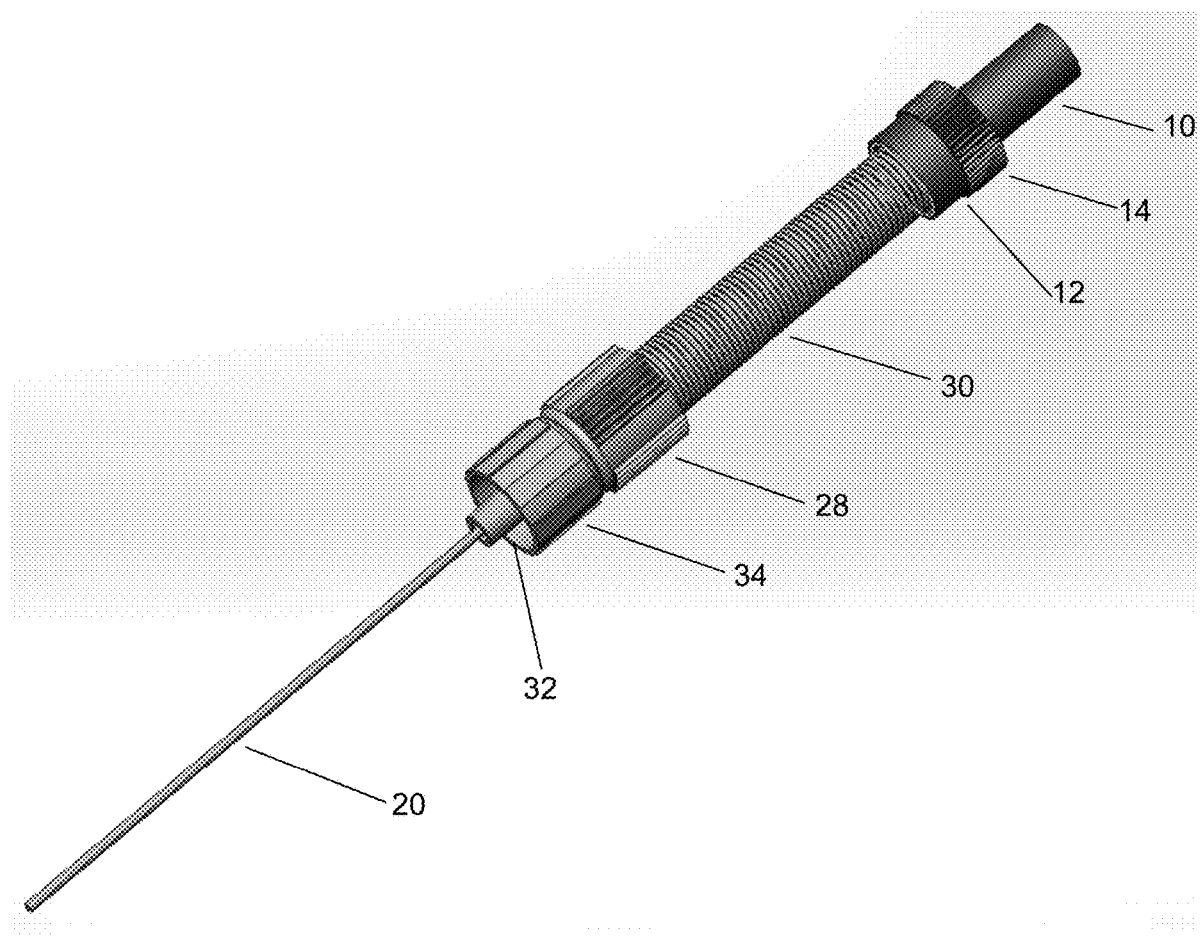
FIG. 5 is a perspective view of the delivery adapter of FIG. 4.

FIGS. 4-5 show another embodiment of a delivery adapter showing an additional distal rotating element 34 which sits just distal of distal connector 28. In one example, bridging piece 30 is glued into proximal connector 12 (e.g., via UV glue) and glued into distal connector 28. Any torquing of the proximal connector 12 by the user prior to attaching the adapter to the catheter hub will result in twisting of distal connector 28. In one embodiment, distal rotating element 34 is free to rotate independent of and/or relative to distal connector 28. The rotational capability of element 34 eases some of the stress on spring bridging element 30 that can otherwise be caused by unilateral torsional stress which may build up on one part of the spring/bridging element, particularly after the adapter is secured to the catheter hub.

Micro-tube 20 may be comprised of a polymer in one example, or a metallic material in another example.

Another embodiment could utilize a threaded bridging piece 30 instead of the spring bridging piece 30 shown in FIGS. 3-5. The threaded bridging piece 30 could be formed of a metallic or polymeric material and would have threads on the surface.

Figure 6:
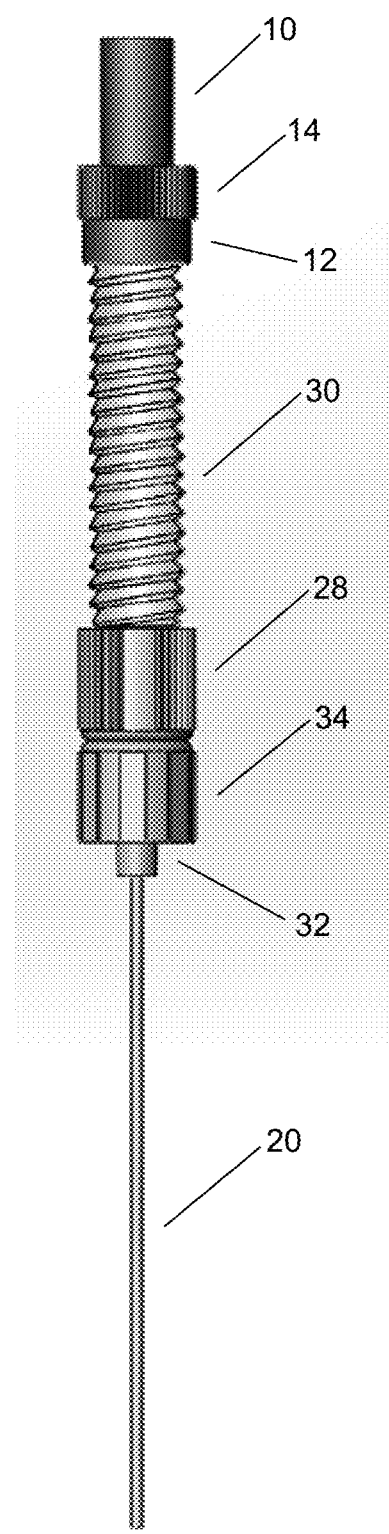
FIG. 6 is a plan view of a delivery adapter according a further embodiment of the present invention.

In one example the bridging piece 30 has external projecting threads and distal connector 28 has corresponding recesses to mate with said threads as shown in FIG. 6, thus rotation of the distal connector 28 will cause upwards or downwards (proximal or distal) movement of distal connector 28. In another example the bridging piece 30 has internal recesses and distal connector 28 has corresponding threads to mate with said recesses, thus rotation of the distal connector 28 will cause upwards or downwards (proximal or distal) movement of distal connector 28. For the embodiment shown in FIGS. 4-5, either distal connector 28 or distal rotating element 34 may have the threads or recesses to mate with the bridging element 30. Alternatively, for the embodiment shown in FIGS. 4-5, both distal connector 28 and distal rotating element 34 may have the threads or recesses to mate with the bridging element 30.

The micro-tube 20 of the embodiments shown in FIGS. 3-5 may terminate within the catheter reservoir 24 or may bypass the catheter reservoir 24 entirely. In one example the distal end of micro-tube 20 extends about 5-40 mm past distal connector 28. In another example the distal end of micro-tube 20 extends about 10-20 mm past distal connector 28. In another example the distal end of micro-tube 20 extends about 15 mm past distal connector 28.

Different catheters have different hub and reservoir sizes. The embodiments shown in FIGS. 3-7 can be thought of as a universal adapter since the micro-tube length does not have to be customized to fit various catheter hubs. Micro-tube 20 is placed as distally as possible within the catheter hub 22. Distal connector 28 and/or distal rotating element 34 is then pulled (spring bridging piece embodiment) or rotated (threaded bridging piece embodiment) so distal connector 28 (FIG. 3 embodiment) or distal rotating element 34 (FIGS. 4-6 embodiment) mates to the catheter hub. When pulled/rotated into this position, the rotating element 34 or distal connector 28 (depending on the embodiment) is then screwed over the catheter hub to secure the connection.

A method of using the universal delivery adapter of FIGS. 3-6 for delivery of a high viscosity liquid (e.g., a liquid embolic) is as follows: The catheter, microcatheter, or delivery device is flushed with saline and navigated to the target site. The catheter is flushed with solvent (e.g., a biocompatible solvent such as DMSO/dimethyl sulfoxide). The catheter hub 22 is filled with solvent (DMSO) in order to remove air bubbles and minimize chances of air bubble formation. The proximal connector 12 of the delivery adapter is connected to the syringe, and liquid embolic is injected through the delivery adapter to purge the delivery adapter of air. Once purged, the micro-tube 20 is placed within the catheter hub 22. Once the micro-tube 20 is placed within the catheter hub 22, the distal connector 28 (FIG. 3 embodiment) and/or distal rotating element 34 (FIGS. 4-6 embodiments) is pulled (spring bridging piece 30) or rotated (threaded bridging piece 30) to connect to the catheter. When pulled/rotated into this position, the rotating element 34 or distal connector 28 (depending on the embodiment) is then screwed over the catheter hub to secure the connection. Liquid embolic may then be delivered from the syringe, via the delivery adapter, to the target treatment site via the catheter once the catheter is navigated to the target treatment site.

Figure 7A:
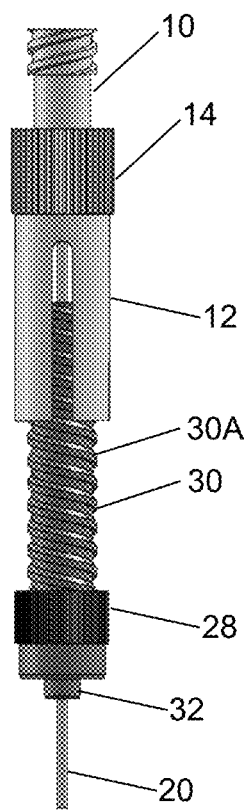
FIG. 7A depict a further embodiment of a delivery adapter according to the present invention.
Figure 7B:
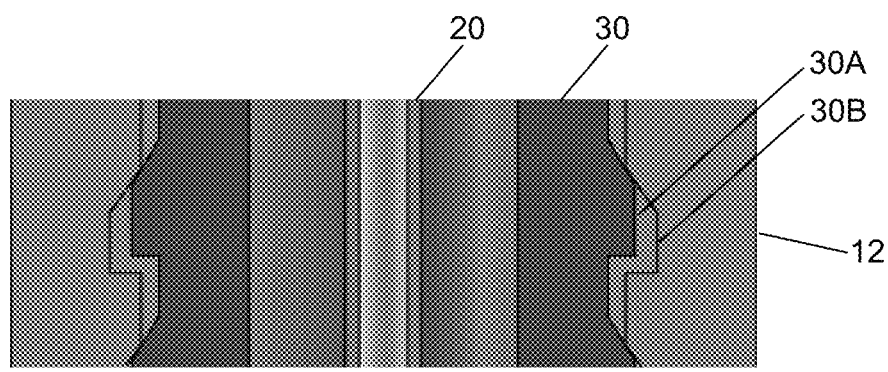
FIG. 7B illustrates a cross-sectional view of a thread configuration of the embodiment of FIG. 7A.

Referring to FIGS. 7A-7B, an additional embodiment of the adapter is shown. Proximal connector 12 mates with threaded bridging piece 30 via external threads 30A on the bridging piece and internal threads 30B on the proximal connector 12. However, the mating surfaces of the threads 30A, 30B are such that a threshold axial force (i.e., up or down) exerted on the proximal connector 12 will cause the walls of the proximal connector 12 to expand and to disengage the threads 30A/30B. This allows axial movement (either up or down) of the proximal connector 12 relative to the threaded bridging piece 30 in a ratchet-type action. Once the threshold axial force is removed, the walls of the proximal connector 12 will return to a normal position and the threads 30A, 30B will re-engage. In one preferred embodiment, the mating surfaces of the threads 30A/30B are ramped as illustrated in FIG. 7B.

In one embodiment, the proximal connector 12 is configured such that the user can squeeze together the outer top edges of the proximal connector 12 and thereby force the lower edges of the proximal connector to flex outwardly.

This results in the disengagement of the threads 30A, 30B and allows the user to move the proximal connector 12 up and down freely. Once the desired position is reached, the user releases outer top edges of the proximal connector 12 and the lower edges of the proximal connector 12 return to the unflexed state and thereby threads 30A/30B reengage. The proximal connector 12 may adopt a slightly concave shape in this embodiment to enable such flexing in response to this squeezing pressure. In one example, a grasping portion (i.e. a roughened portion for the user to grip) can be included on the proximal connector 12 where the user would squeeze to initiate the flexing in order to freely move proximal connector 12.

Continuing to refer to FIGS. 7A, 7B, in use, the user determines the desired distance for the microtube 20 to extend beyond the distal connector 28. The user then exerts an axial force on the proximal connector 12 in the manner described above to move the proximal connector 12 and its attached microtube 20 to the aforesaid distance. The user can "fine tune" the desired distance through rotation of the proximal connector 12 relative to the threaded bridge piece 30. The adapter is then ready for inserting the microtube 20 into the catheter hub. The user then fastens the catheter to the adapter via screwing the distal connector 28 onto the catheter hub (e.g., via a luer lock connection). The user also attaches the syringe to the luer lock 10 at the top of the proximal connector 12.

Figure 8:
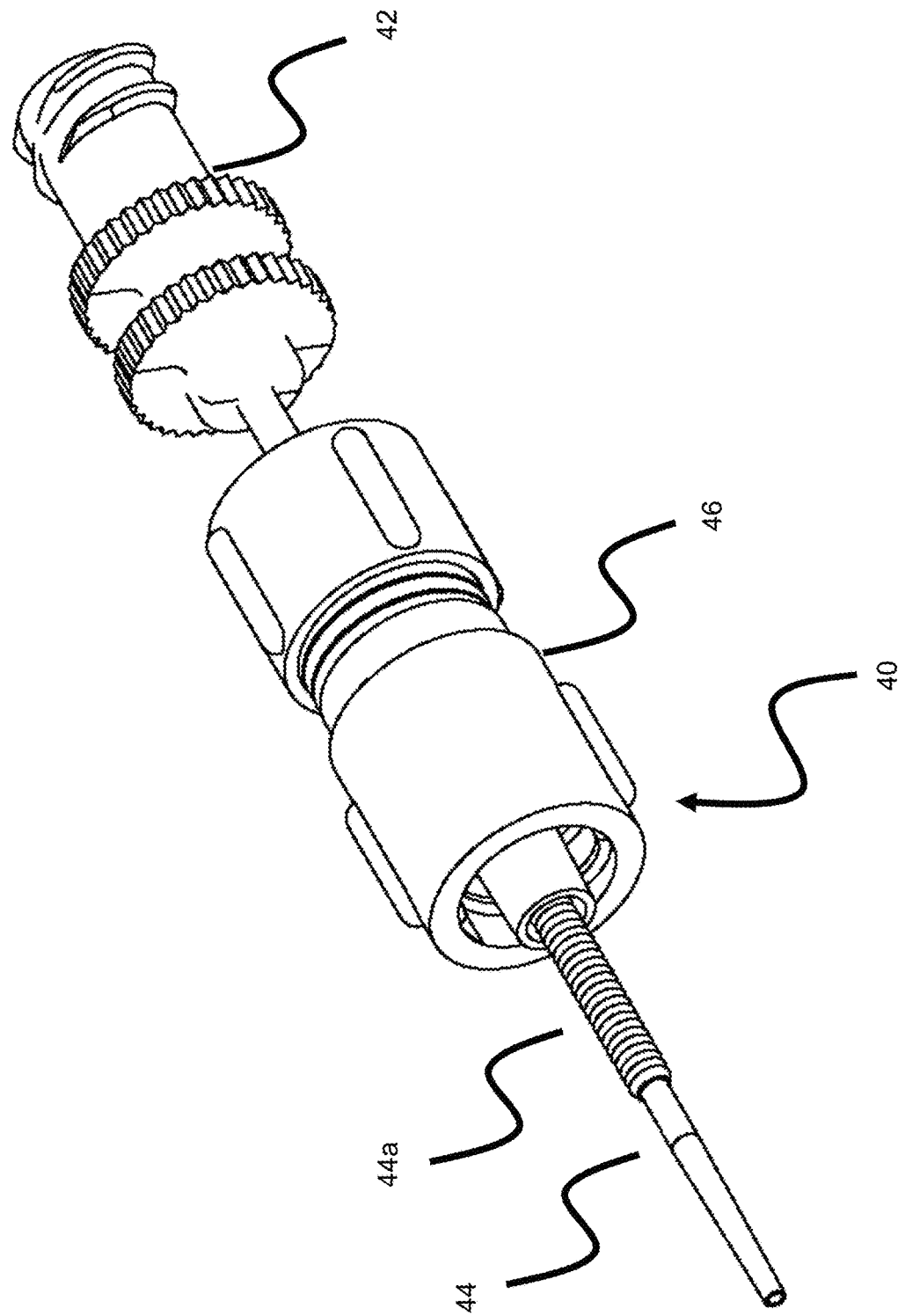
FIG. 8 illustrates a delivery adapter according to another embodiment of the present invention.
Figure 9:
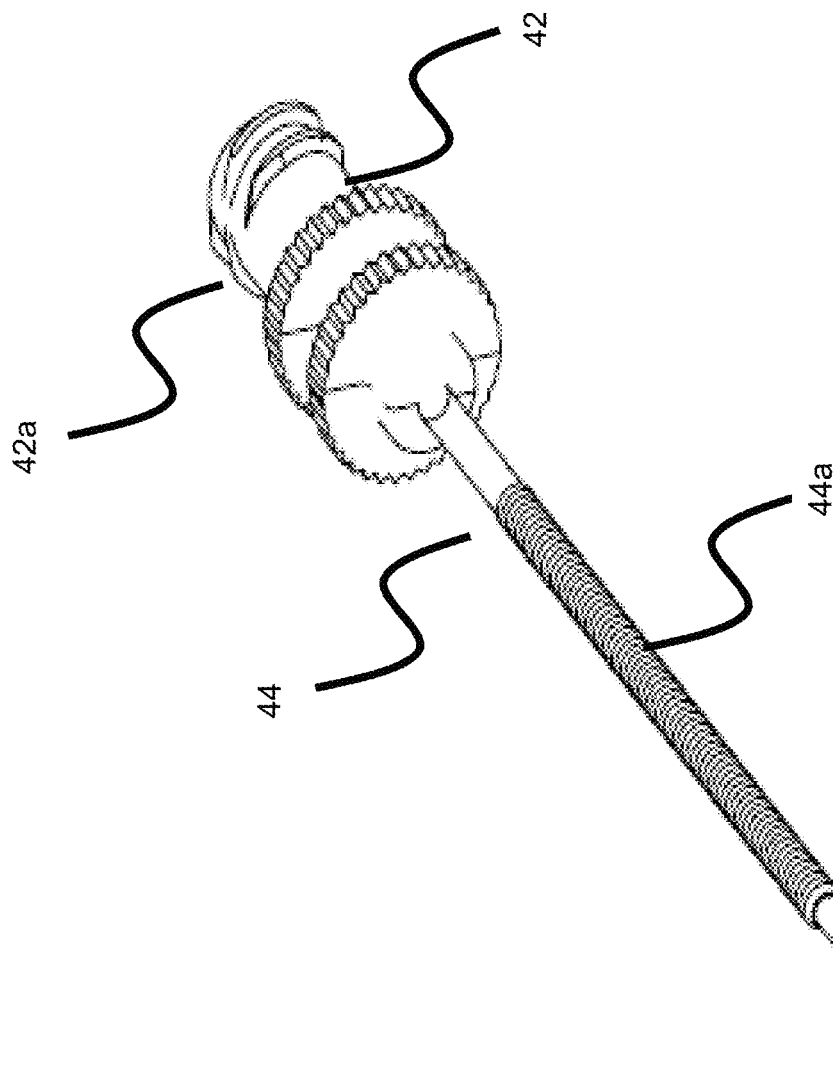
FIGS. 9-10 illustrate the proximal connector and micro-tube portions of the delivery adapter of FIG. 8.
Figure 10:
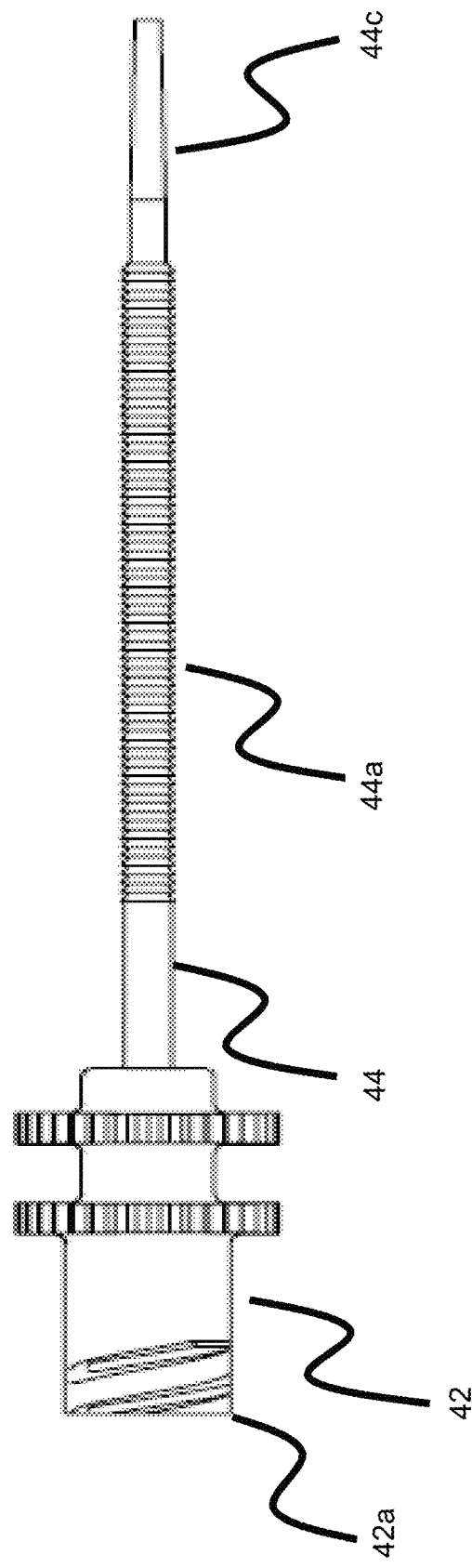
Figure 11:
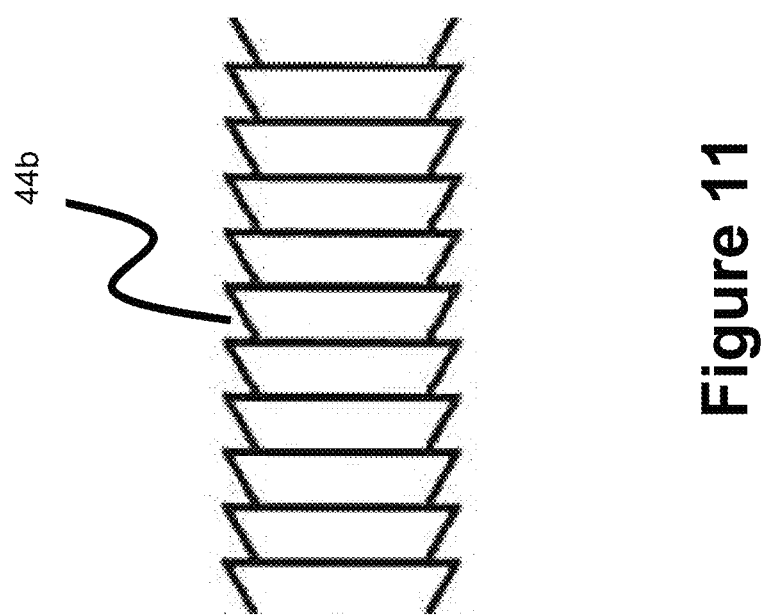
FIG. 11 illustrates a portion of a micro-tube used in a delivery adapter, wherein the micro-tube has a number of elements used to retain a distal connector.

FIGS. 8-15 show a universal delivery adapter according to another embodiment of the invention. Proximal connector 42, which is at a proximal portion of the adapter 40, is adapted to connect to a syringe which contains liquid embolic, as shown in FIG. 8. The proximal connector can contain threads 42a or other connective elements to enable connection with the syringe through rotational engagement. A micro-tube 44 (similar to micro-tube 20 of the previous embodiments) connects to the proximal connector 42 and functions as a conduit for embolic passage from the syringe which travels through micro-tube 44. In one example, micro-tube 44 is metallic, though other materials including polymers can be used. FIGS. 9-10 offer another view of proximal connector 42 and micro-tube 44.

Micro-tube 44 has a series of elements 44a over a portion of its length. These elements 44a can take on various forms and/or shapes. In one embodiment, these elements 44a are circular threads. In another embodiment shown in FIG. 11, elements 44a are configured as angled tapers 44b. In some embodiments, these angled tapers 44b are serrations. In some embodiments generally shown in the Figures, these elements 44a have a larger diameter than the rest of micro-tube 44 and thereby radially project outward relative to the rest of micro-tube 44 so as to result in a thickened region of the micro-tube. In other embodiments, these elements 44a have the same or smaller diameter than the rest of micro-tube 44—for instance, the region of the micro-tube containing elements 44a can have a smaller inner diameter compared to the rest of the micro-tube, where the projecting elements 44a then span radially outwards so as to substantially match the outer diameter of the rest of the micro-tube. In one preferred embodiment, the majority of micro-tube 44a has a relatively consistent outer diameter and elements 44a are fashioned as tapered cuts within a substantial length of micro-tube 44; in this way, the tapered down areas represent smaller outer diameter regions, while the radially-flared part of the tapers are substantially equal to the rest of the outer diameter of micro-tube 44. In one embodiment, the distal section of micro-tube 44 is thinned in order to facilitate placement through or past the catheter reservoir.

A distal connector 46 sits over the micro-tube. Distal connector 46 adopts a first configuration where the distal connector 46 is movable over micro-tube 44, and a second configuration where the distal connector 46 is fixed relative to micro-tube 44. Where distal connector 46 adopts this second, fixed configuration, elements 44a help secure the distal connector 46 in a fixed manner relative to the overall micro-tube 44, in a manner that will be explained in more detail.

Figure 12:
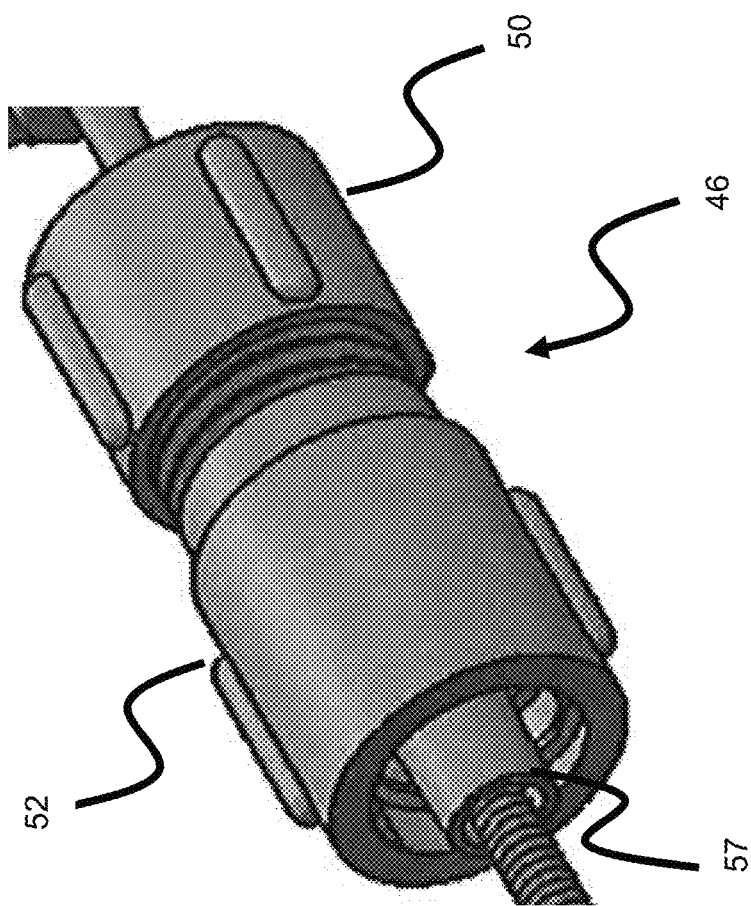
FIG. 12 illustrates a distal connector used in the delivery adapter of FIG. 8.
Figure 13:
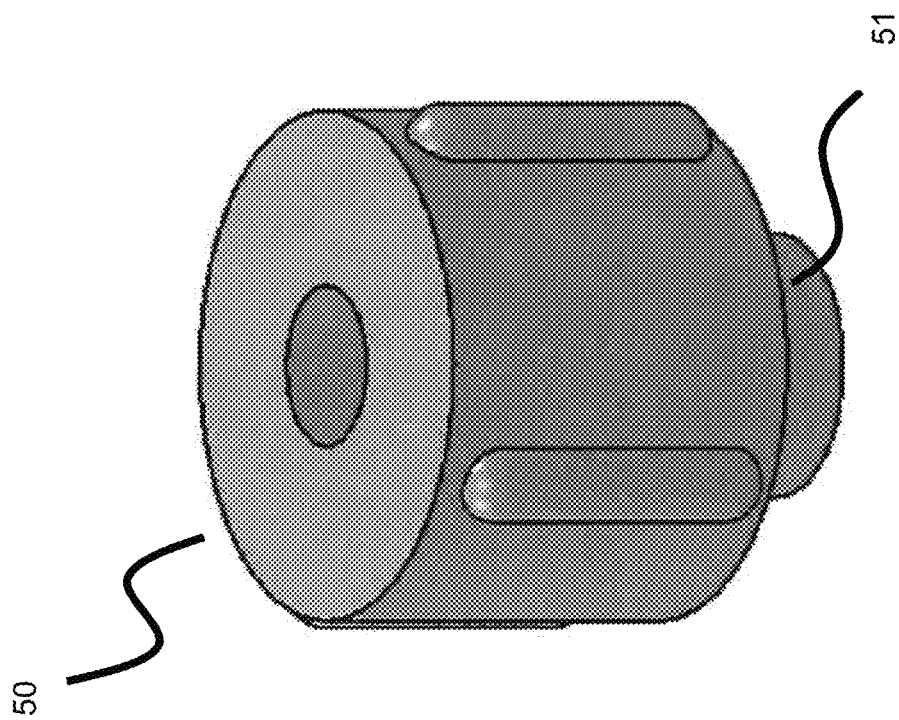
FIG. 13 illustrates a cap piece used in the distal connector of FIG. 12.

Distal connector 46, shown in more detail in FIG. 12, can function in a manner like a traditional Tuohy-Borst adapter and comprises a cap piece 50 and a base piece 52. Cap piece 50 and base piece 52 are shown in more detail in FIGS. 13-14. The distal portion of base piece 52 is adapted to mate with the catheter hub (e.g., through threads and corresponding recesses enabling rotational engagement) while the cap piece 50 and base piece 52 are adapted to mate together. In one example a portion of the base piece has threads 54 which mate with corresponding recesses within the cap 50 such that the cap can be tightened with respect to the base piece 52—thereby enabling rotational engagement. The cap piece 50 includes a projecting element 51 that projects into the base piece 52 when said cap piece 50 and said base piece 52 are mated together. Cap piece 50 and base piece 52, which together comprise distal connector 46, both include a lumen which provide a passage to accommodate micro-tube 44.

Figure 14A:
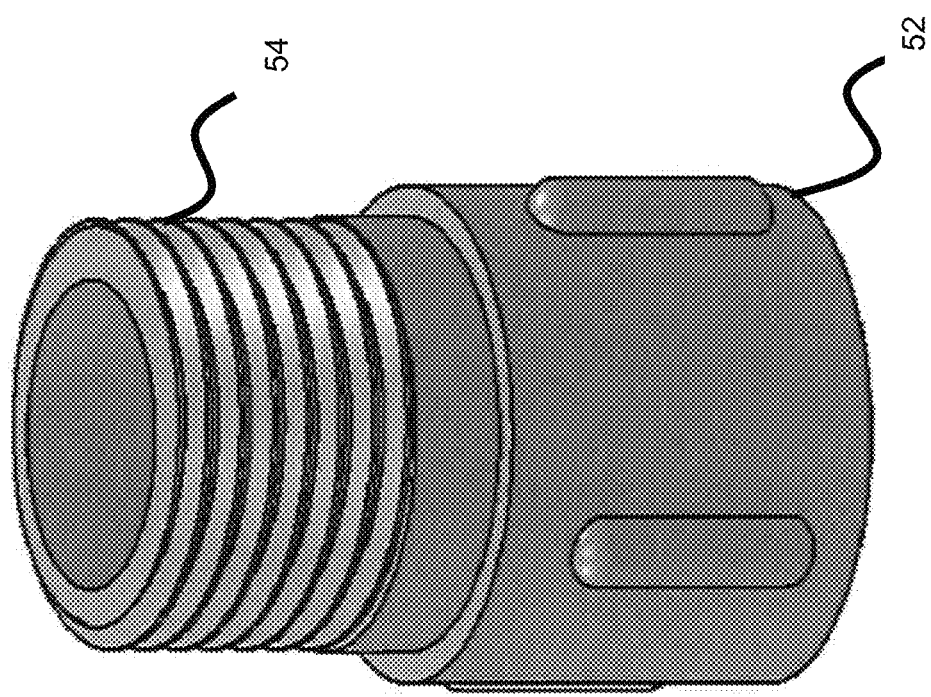
FIGS. 14a-14b illustrate a base piece used in the distal connector of FIG. 12.
Figure 15:
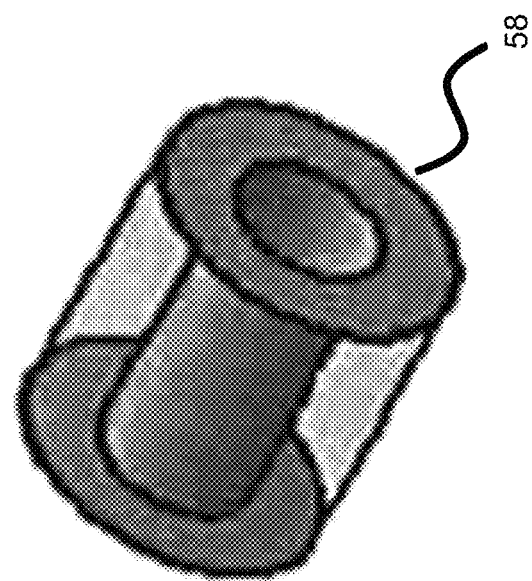
FIG. 15 illustrates a seal used in the distal connector of FIG. 12.
Figure 14B:
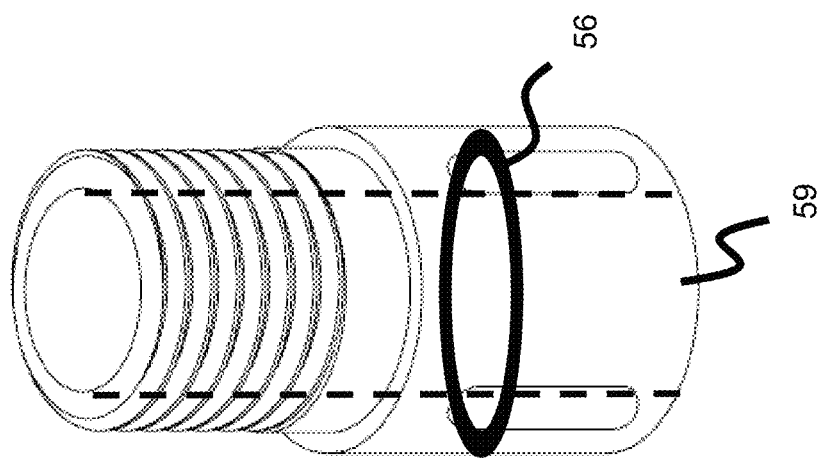

Base piece 52, shown in FIGS. 14a-14b, includes an internal waist or rim 56 shown in FIG. 14b. This waist or rim can be thought of as an internal projection but does not interfere with the inner lumen 59 which accommodates passage of micro-tube 44 since the internal waist/rim still leaves a large enough lumen to accommodate the diameter of micro-tube 44—as shown in FIG. 14b. Seal element 58, shown in FIG. 15, sits on top of this waist or rim. In one example, the waist sits on the lower half of base piece 52 (e.g., toward the lower, thicker section of base piece 52 of FIGS. 14a-14b). Seal element 58 functions to lock to elements 44a of micro-tube 44, which in turn locks distal connector 46 to micro-tube 44, thereby locking the position of the distal connector. Seal element 58 is preferably flexible. In one example the seal element is comprised of a cylindrical silicone piece with a lumen therein which is snug compared to micro-tube 44 and thereby accommodates micro-tube 44. This shape can be thought of as an annular cylinder due to the lumen or annulus within the cylindrical shape. The inner diameter of seal element 58 is close to the diameter of elements 44a and thereby contacts elements 44a. In other embodiments, seal 58 can be slightly oversized relative to elements 44a such that it will not contact said elements 44a. Base piece 52 further includes a distal projecting tubular element 57 connected to waist 56 which accommodates micro-tube 44, as shown in FIG. 12.

When cap piece 50 is tightened with respect to base piece 52, projecting element 51 of cap piece 50 starts to contact seal 58. Seal 58 is pinched in response which causes at least a portion of the seal to deform such that the seal's inner diameter narrows and directly pushes into elements 44a of micro-tube 44. As cap piece 50 is further tightened, seal 58 deforms further thereby resulting in more radial contact friction and contact force between elements 44a and seal 58. At some point, this contact force will effectively lock seal 58 to elements 44a, as the pulling force exerted by the user will need to be progressively greater and greater to overcome this contact force. When cap piece 50 is completely tightened with respect to base piece 52 so that further tightening is no longer possible, projecting element 51 will exert its axial maximum force on seal 58 thereby deforming seal 58 to its maximum extent—meaning the inner diameter of seal 58 will be at its narrowest thereby exerting significant force on elements 44a thereby locking or fixing seal 58 to micro-tube's 44 elements 44a. When seal 58 is in this fixed or locked configuration, the overlying distal connector 46 will, in turn, be locked in position over micro-tube 44.

When cap piece 50 is loosened with respect to base piece 52, the pinch of seal 58 is released and the distal connector can freely move in either direction over the micro-tube since seal 58 is not locked or fixed in place. In this way, tightening cap piece 50 relative to base piece 52 deforms seal 58 so as to lock seal 58 relative to micro-tube 44—which in turns locks the whole distal connector 46 to micro-tube 44.

In some embodiments, as discussed above, elements 44a of micro-tube 44 can take on the form of angled tapers or serrations. In these embodiments, the angled tapers or serrations would project into the deformable seal 58 thereby helping to lock the seal 58 in place as seal 58 deforms in response to cap piece 50 being tightened relative to base piece 52, in turn locking the distal connector 46.

In some embodiments, the interior channel of the cap piece can include a corresponding surface to mate with elements 44a of micro-tube 44—for instance elements 44a could function as threads and the cap piece could include corresponded recesses to mate with these threads. In other embodiments, the cap piece contains no such corresponding surface, and instead the elements 44a of micro-tube 44 simply act as an enlarged surface to contact seal 58 in order to lock distal connector 40 to micro-tube 44, in the manner described above.

Seal 58 provides another benefit besides creating a flexible locking interface to lock the position of distal connector 46. Any open space within the distal connector can allow liquid or embolic reflux in situations where there is embolic spraying or backflow during delivery. Since the cylindrical seal 58 is flexible and pinches against micro-tube 44, the seal 58 seals any open space between micro-tube 44 and base piece 52 when distal connector 46 is locked, preventing any embolic reflux during delivery from migrating back into the delivery adapter. Any embolic would be caught by the seal itself since seal 58 fills the radial channel between micro-tube 44 and base piece 52. In this way, seal 58, in additional to locking distal connector 46 to micro-tube 44, also functions as a mechanism to ensure embolic will not reflux or pass through the delivery adapter.

The method of use of this embodiment is similar to the previous embodiments. The distal end of the micro-tube 44 is placed into the catheter hub. Base piece 52 is then mated with the catheter hub. Cap piece 50 is then mated with respect to base piece 52, which in turn locks seal 58 so that the distal connector 46 is fixed with respect to micro-tube 44. Proximal connector 42 is connected to a syringe and the system is configured so that the syringe can deliver liquid embolic (or other material) through the catheter.

Often with liquid embolic procedures, multiple syringes need to be used. For instance, a first syringe with DMSO is initially used to purge the catheter hub of fluid and a second syringe with the embolic material is subsequently used. Sometimes multiple syringes of embolic material need to be used, for instance in situations where the target treatment area is particularly large. The operating physician will have to physically remove one syringe and physically couple another syringe which can add to the treatment procedure time. The following embodiments utilize an adapter with a multiple-port manifold so that multiple syringes can be coupled to a common adapter.

Figure 17:
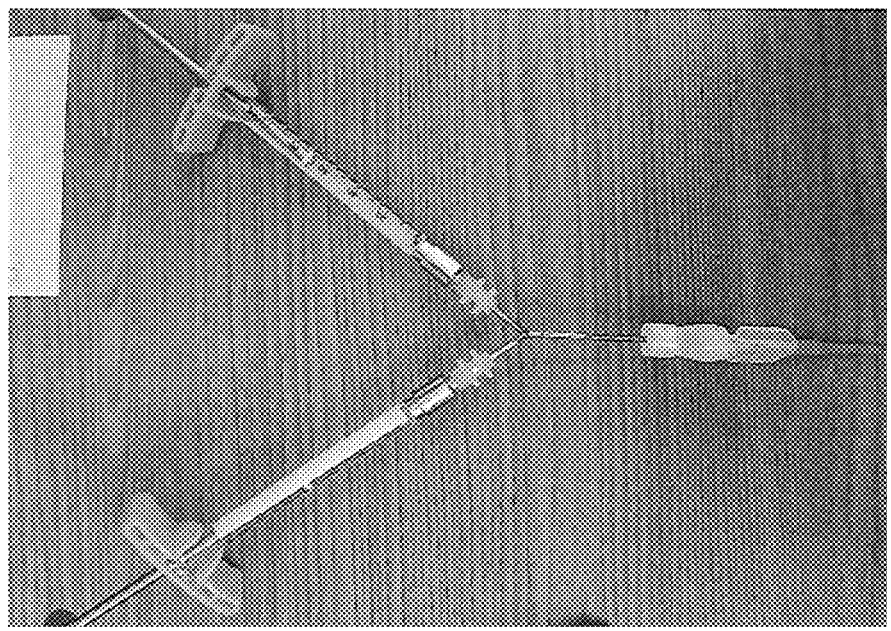
FIGS. 16-17 illustrate a delivery adapter with two ports to accommodate two syringes.
Figure 16:
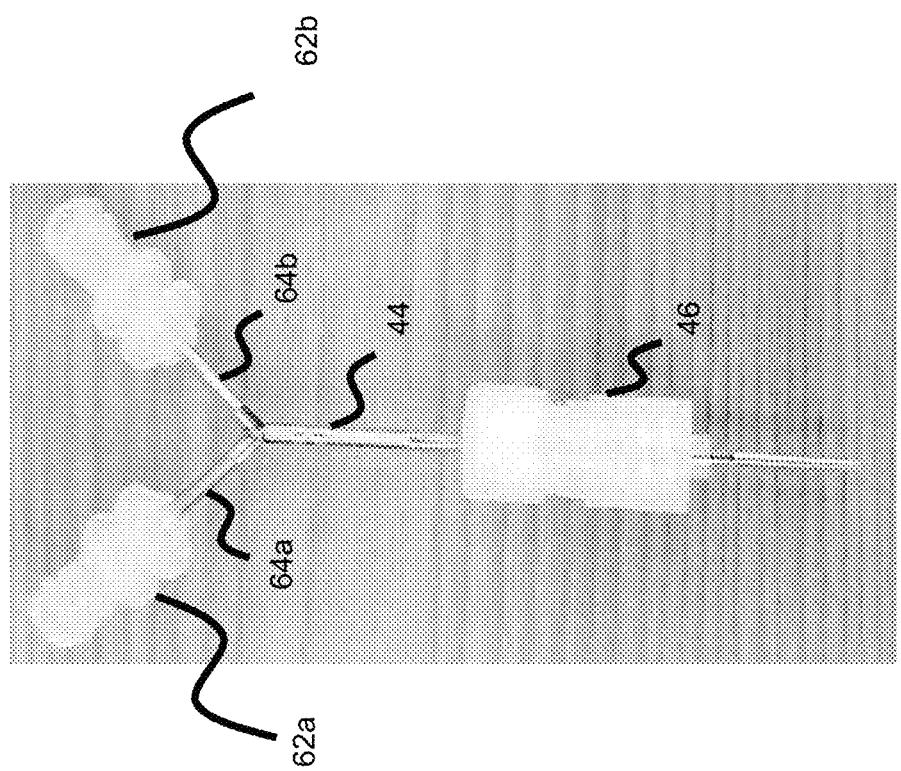

FIG. 16 shows an embodiment of a multiple-port manifold for multiple syringes. Two proximal connectors/ports 62a, 62b provide a connection point for syringes. The proximal connectors are designed and function similar to proximal adapter 42 of FIG. 8. Port conduit tubes 64a and 64b connect to the ports and intersect micro-tube 44 such that the internal passage of the port conduit tubes 64a and 64b connect to micro-tube 44. In one example, port conduit tubes 64a and 64b are welded to micro-tube 44. In another example, the port conduit tubes are built over micro-tube 44. Distal connector 46 sits over a distal portion of micro-tube 44 and operates like the distal connector 46 described and shown earlier in FIGS. 8-15. In operation, the user would connect one syringe to each connector 62a, 62b as shown in FIG. 17—for example, one syringe could contain DMSO and the other syringe could contain embolic. The user would first expel DMSO from the DMSO-only syringe to clear the catheter hub and catheter of residual material. Instead of disconnecting the DMSO syringe, connecting an embolic syringe, and then expelling embolic from the embolic syringe, the user would then expel embolic from the other embolic containing syringe, in turn decreasing procedure times.

Figure 18:
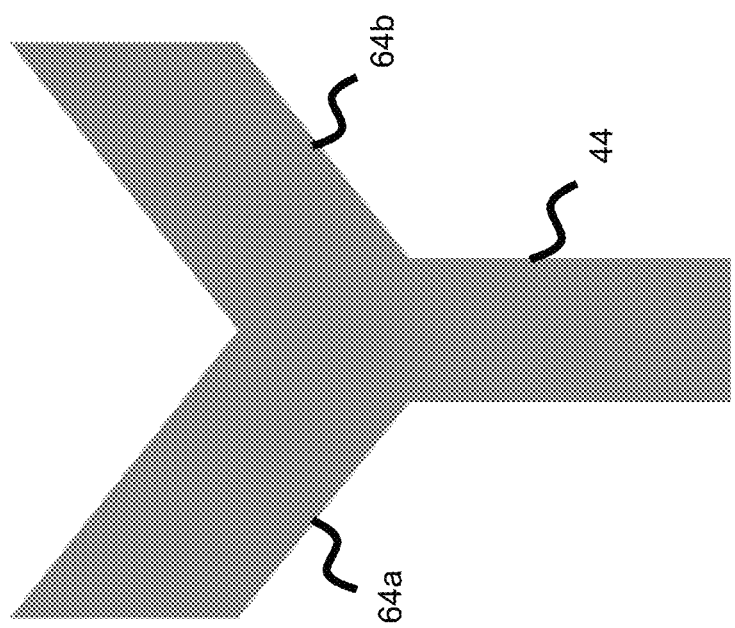
FIG. 18 illustrates the interface between various ports of the delivery adapter of FIGS. 16-17.

FIG. 18 shows the intersection points between micro-tube 44 and conduit tubes 64a, 64b (which connect respectively to proximal connectors 62a, 62b). Since three tubular elements come together in this region, there is a risk that in some circumstances (e.g., where a user expels the syringe contents at a high rate by depressing the syringe plunger with high force) that fluid travelling through conduit 64a into micro-tube 44 could incidentally traverse partially or completely through conduit 64b. In one embodiment, the intersection region between tubes 64a, 64b, and 44 could contain a check valve to prevent backflow through the tube. A check valve would allow flow in only one direction (i.e. distally through micro-tube 44) while preventing backflow. In another embodiment, each port conduit tube 64a, 64b would contain its own check valve to prevent backflow so that fluid being delivered from one syringe could not migrate through the conduits into the other syringe.

Though the multiple-syringe port concept was primarily shown with regards to the delivery adapter configuration of FIGS. 8-15, other embodiments could utilize the various other adapter configurations shown and described earlier in FIGS. 1-7. The primary focus of these embodiments utilizes the multiple port manifold that enables multiple syringes to be connected at the same time.

Figure 20:
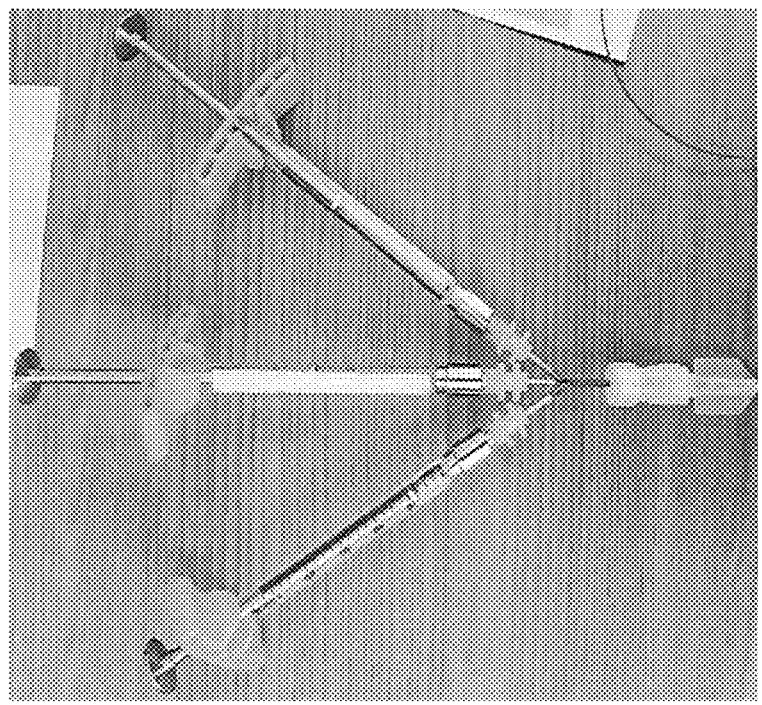
FIGS. 19-20 illustrate a delivery adapter with three ports to accommodate three syringes.
Figure 19:
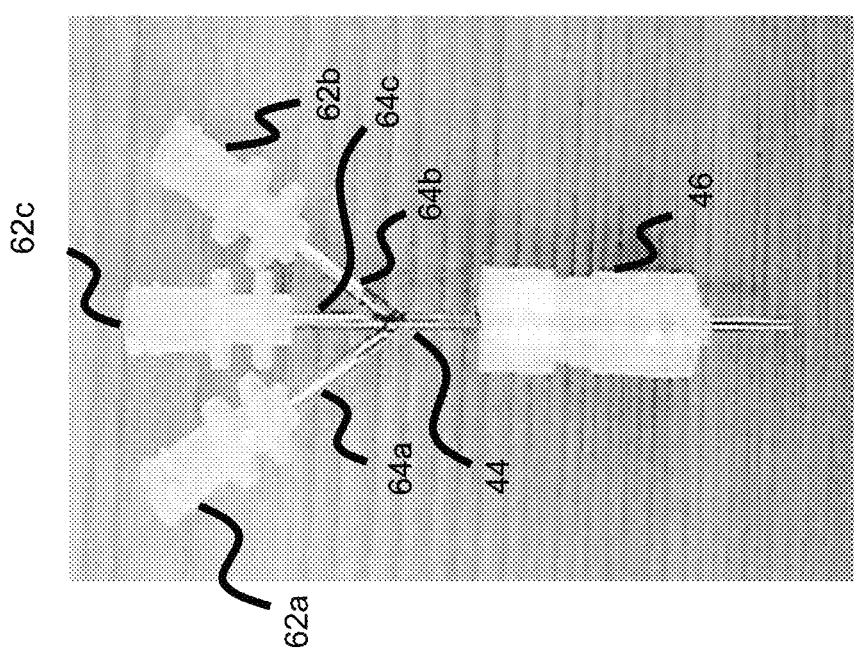
Figure 21:
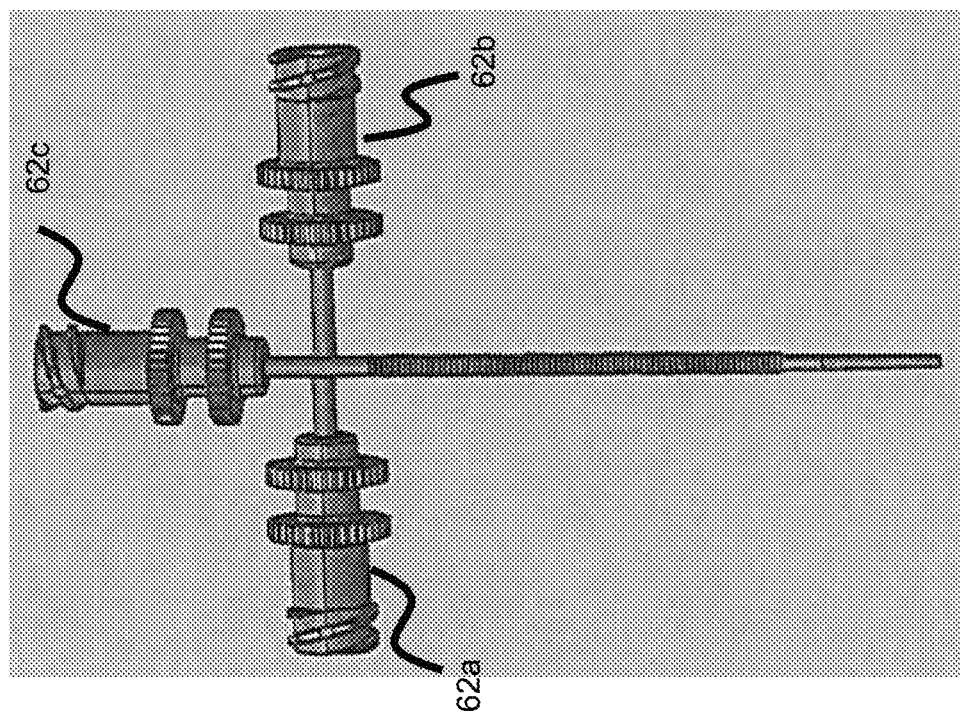
FIG. 21 illustrates an alternative version of a delivery adapter with three ports to accommodate three syringes.

FIGS. 19-20 show another embodiment utilizing three ports 62a-62c and three associated conduit tubes 64a-64c, which in turn allow for three syringes to be connected. FIG. 21 shows still another embodiment utilizing three ports where the connector/ports 62a-62c are offset about 90 degrees from each other. Different embodiments could utilize more than three ports.

In another embodiment, a kit of parts includes any of the universal delivery adapter embodiments shown/described above and presented herein, and one or more syringes of liquid embolic material such as the liquid embolic described in U.S. Pat. Nos. 9,078,950 and 9,655,989, both of which are hereby incorporated by reference in their entirety. With these kits, the user would have the ability to use liquid embolic material with catheter hubs of different sizes. Currently, many manufacturers sell liquid embolic material with various sized delivery adapters included so the liquid embolic can be used with catheter hubs of different sizes. With the universal delivery adapter embodiments presented herein which allow one universal adapter to be used with different sized catheters/catheter hubs, a kit could simply include liquid embolic material and a universal adapter to fit a range of catheter hubs. In another embodiment, a kit of parts includes any of the universal adapter embodiments shown/described above and presented herein, one or more syringes of liquid embolic material, and one or more syringes of DMSO. In this embodiment, the end user would have everything needed to conduct a liquid embolic procedure in one kit—a universal adapter to fit various catheter hub sizes, liquid embolic to embolize the target site, and DMSO to flush the catheter/catheter hub to help prevent early embolization of the liquid embolic material. In another embodiment, a kit of parts includes any of the universal adapter shown/described above and presented herein, one or more syringes of liquid embolic, one or more syringes of DMSO, and one or more syringes of saline.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An adapter comprising:
   a first connector adapted for connection to a syringe;
   a tube extending from the first connector and being sized and positioned for placement in a catheter;
   a second connector adapted for connection to a catheter hub, the second connector having a lumen accommodating the tube;
   wherein the second connector has a first configuration where it is freely movable over the tube and a second configuration where it is not freely movable over the tube and is pinched against to directly engage with projecting elements on an outer surface of the tube to control how much of the tube extends distally beyond the second connector.

2. The adapter of claim 1 wherein the second connector includes a cap piece releasably engaged with a base piece.

3. The adapter of claim 2 wherein the cap piece is rotationally engaged with the base piece.

4. The adapter of claim 1 wherein the projecting elements are angled tapers.

5. The adapter of claim 1 wherein the second connector includes a seal which engages with the tube's projecting elements thereby fixing the second connector in place.

6. The adapter of claim 5 wherein the seal is a flexible annular cylinder.

7. An adapter comprising:
   a first connector adapted for connection to a syringe;
   a tube extending from the first connector and being sized and located for placement in a catheter;
   a second connector adapted for connection to a catheter hub, the second connector having a lumen accommodating the tube;
   wherein the second connector further comprises a seal;
   wherein the seal has a first configuration where the seal is freely movable over the tube and a second configuration where the seal is not freely movable over the tube and is pinched against to directly engage elements on an outer surface of the tube, thereby controlling how much of the tube extends distally beyond the second connector.

8. The adapter of claim 7 wherein the second connector includes a cap piece releasably engaged with a base piece.

9. The adapter of claim 8 wherein the cap piece is rotationally engaged with the base piece.

10. The adapter of claim 7 wherein the seal is a flexible annular cylinder.

11. The adapter of claim 7 wherein the seal is a silicone cylindrical element with a lumen therein.

12. The adapter of claim 7 wherein the elements comprise projecting elements.

13. The adapter of claim 12 wherein the projecting elements are angled tapers.

14. An adapter comprising:
    a first connector adapted for connection to a syringe;
    a tube extending from the first connector and being sized and positioned for placement in a catheter;
    a second connector adapted for connection to a catheter hub, the second connector having a lumen accommodating the tube, the second connector further including a cap piece releasably fixed to a base piece;
    wherein the second connector is fixed to and directly engages an outer surface of the tube when the cap piece is in a tightened position relative to the base piece, and wherein the second connector is freely movable over the tube when the cap piece is in a loosened position relative to the base piece, thereby controlling how much of the tube extends distally beyond the second connector; and,
    wherein the cap piece is rotationally engaged with the base piece.

15. The adapter of claim 14 wherein the tube includes projecting elements.

16. The adapter of claim 15 wherein the projecting elements are angled tapers.

17. The adapter of claim 15 wherein the second connector includes a seal which engages with the tube's projecting elements thereby fixing the second connector in place.

18. The adapter of claim 17 wherein the seal is a flexible annular cylinder.

* * * * *